(12) United States Patent
Xia

(10) Patent No.: US 7,416,747 B2
(45) Date of Patent: Aug. 26, 2008

(54) HERBAL COMPOSITION FOR TREATMENT OF NEURODEGENERATION AND NEURONAL DYSFUNCTION

(76) Inventor: YongChao Xia, Provincial Hospital of Chinese Medicine, LanZhou 730050, GanSu Province (CN)

( * ) Notice: Subject to any disclaimer, the term of this patent is extended or adjusted under 35 U.S.C. 154(b) by 0 days.

(21) Appl. No.: 11/735,101

(22) Filed: Apr. 13, 2007

(65) Prior Publication Data

US 2007/0178178 A1 Aug. 2, 2007

Related U.S. Application Data

(63) Continuation-in-part of application No. 10/442,865, filed on May 22, 2003, now Pat. No. 7,205,004, which is a continuation of application No. PCT/IB01/02859, filed on Nov. 21, 2001.

(60) Provisional application No. 60/253,013, filed on Nov. 22, 2000.

(51) Int. Cl.
*A61K 36/232* (2006.01)
*A61K 36/236* (2006.01)
*A61K 36/481* (2006.01)
*A61K 36/484* (2006.01)
*A61K 36/487* (2006.01)
*A61K 36/533* (2006.01)
*A61K 36/8969* (2006.01)

(52) U.S. Cl. .................... 424/725; 424/757
(58) Field of Classification Search ............ None
See application file for complete search history.

(56) References Cited

U.S. PATENT DOCUMENTS 7,205,004 B2 4/2007 Xia

OTHER PUBLICATIONS http://www.centerwatch.com/cgi-bin/cl.pl?p=patient/studies/stu121332.html&h=msfocushead.txt&f=msfocusfoot.txt.*
http://www.nationalmssociety.org/site/PageServer?pagename=HOM_LIVE_treatments.*
http://www.centerwatch.com/cgi-bin/cl.pl?p=patient/studies/stu121332.html&h=msfocushead.txt&f=msfocusfoot.txt—accessed Feb. 2008.*
http://www.nationalmssociety.org/site/PageServer?pagename=HOM_LIVE_treatments—accessed Feb. 2008.*
Chinese Patent Application No. 96122265.4, May 27, 1998, YongChao Xia. "Bu-Nao-Gao".
Chinese Patent Application No. 199119227.3, Mar. 8, 2000, Zhan Shan Guo. "Medicinal Wine for treating hyperlipidemia and high blood-viscosity".
Chinese Patent Application No. 93106328.0, May 11, 1994, Qishong Gao and Haifeng Suen "Method of preparation for Flaccidity Recovery".
"The Chinese Materia Medica", edited by Beijing University of Traditional Chinese Medicine, Jun. 1984, pp. 208-209, 211-212.
PCT International Preliminary Examination Report, Jun. 12, 2003 for Yongchao Xia, PCT/IB01/02859, "Herbal Composition For Treatment of Neuronal Injuries and Neuronal Degeneration, Methods to Prepare the Same and Uses Thereof."
PCT International Search Report Examination Report, Oct. 3, 2002, for YongChao Xia, PCT/IB01/02859, "Herbal Composition for Treatment of Neuronal Injuries and Neuronal Degeneration, Methods to Prepare the Same and Uses Thereof."
CN A1182603, May 27, 1998, The Traditional Chinese Medical Hospital of Gansu.
CN A1086430, May 11, 1994, Gao, Qishong.
CN A1246368, Mar. 8, 2000, Guo, Zhanshan.
Chinese Patent Application No. 99119227.3, Mar. 8, 2000, Zhan Shan Guo. "Medicinal Wine for treating hyperlipidemia and high blood-viscosity".

* cited by examiner

*Primary Examiner*—Susan C Hoffman
(74) *Attorney, Agent, or Firm*—Law Offices of Albert Wal-Kit Chan, PLLC

(57) ABSTRACT

This invention provides methods of using various herbal compositions to treat neurodegenerative diseases and neuronal dysfunctions, said compositions comprise a combination of *Radix angelica sinensis* (DangGui), *Ligusticum chuanxiong* (ChuanXiong), *Hirudo* (ShuiZhi), *Polygonatum sibiricum* (HuangJing), *Carthamus tinctorius* (Hong Hua), *Astragalus membranaceus* (HuangQi), and *Glycyrrhiza uralensis* (Gancao).

6 Claims, No Drawings

HERBAL COMPOSITION FOR TREATMENT OF NEURODEGENERATION AND NEURONAL DYSFUNCTION

CROSS-REFERENCE TO RELATED APPLICATIONS

This is a continuation-in-part application of U.S. Ser. No. 10/442,865, filed May 22, 2003, now U.S. Pat. No. 7,205,004 which is a continuation application of International Application PCT/IB01/02859, filed Nov. 21, 2001, which claims priority of U.S. Ser. No. 60/253,013, filed Nov. 22, 2000. The entire contents and disclosures of the preceding applications are incorporated by reference into this application.

Throughout this application, various references or publications are cited. Disclosures of these references or publications in their entireties are hereby incorporated by reference into this application in order to more fully describe the state of the art to which this invention pertains.

FIELD OF THE INVENTION

This invention relates to methods of using herbal compositions to treat neuronal injuries, neuronal dysfunction and neurodegeneration.

BACKGROUND OF THE INVENTION

BuNaoGao (BNG) is a cocktail of Chinese medicine. This formulation consists of 14 ingredients and was invented by Dr. YongChao Xia (Provincial Hospital of Chinese medicine. LanZhou, P.R. China). BuNaoGao was designed to treat various forms of neuronal injuries and neuronal dysfunctions and neurodegeneration, i.e. head, and spinal cord injury, cerebral palsy, motor neuron diseases (1-5). The early explorative clinical work was carried out in Chinese patient population in the late 70's and early 80's. BuNaoGao clinical trials for the treatment of head spinal cord injury, motor neuron diseases and other forms of degenerative diseases were carried out in China during the period of 1989-1994 (5). Results of the BuNaoGao clinical trial had gone through peer reviewed process in 1994 and had since acquired the regulatory approval from the Chinese government for human use under supervision.

The present invention report results of using BuNaoGao in treating various forms of neuronal injuries, neuronal dysfunction and neurodegeneration.

SUMMARY OF THE INVENTION

In one embodiment, the present invention provides a method of treating neuronal injuries, neuronal dysfunction and neurodegeneration, comprising the step of administering to a patient in need thereof a compositing comprising *Radix angelica sinensis* (DangGui), *Ligusticum chuanxiong* (ChuanXiong), *Hirudo* (Shuizhi), and *Polygonatum sibiricum* (Huangjing), wherein the g/kg body weight dosages can be increased up to 2.5 times if the body weight of the patient is less than 40 kg.

In another embodiment, the present invention provides a method of treating neuronal injuries, neuronal dysfunction and neurodegeneration, comprising the step of administering to a patient in need thereof a compositing comprising *Radix angelica sinensis* (DangGui), *Carthamus tinctorius* (Hong Hua), *Hirudo* (Shuizhi), and *Polygonatum sibiricum* (HuangiJing), wherein the g/kg body weight dosages can be increased up to 2.5 times if the body weight of the patient is less than 40 kg.

In another embodiment, the present invention provides a method of treating neuronal injuries, neuronal dysfunction and neurodegeneration, comprising the step of administering to a patient in need thereof a compositing comprising *Radix angelica sinensis* (DangGui), *Ligusticum chuanxiong* (ChuanXiong), *Hirudo* (ShuiZhi), *Polygonatum sibiricum* (HuangJing), and *Astragalus membranaceus* (HuangQi), wherein the g/kg body weight dosages can be increased up to 2.5 times if the body weight of the patient is less than 40 kg.

In another embodiment, the present invention provides a method of treating neuronal injuries, neuronal dysfunction and neurodegeneration, comprising the step of administering to a patient in need thereof a compositing comprising *Radix angelica sinensis* (DangGui), *Carthamus tinctorius* (Hong Hua), *Hirudo* (ShuiZhi), *Polygonatum sibiricum* (HuangJing), and *Astragalus membranaceus* (HuangQi), wherein the g/kg body weight dosages can be increased up to 2.5 times if the body weight of the patient is less than 40 kg.

In another embodiment, the present invention provides a method of treating neuronal injuries, neuronal dysfunction and neurodegeneration, comprising the step of administering to a patient in need thereof a compositing comprising *Radix angelica sinensis* (DangGui), *Ligusticum chuanxiong* (ChuanXiong), *Hirudo* (Shuizhi), *Polygonatum sibiricum* (Huangjing), and *Glycyrrhiza uralensis* (Gancao), wherein the g/kg body weight dosages can be increased up to 2.5 times if the body weight of the patient is less than 40 kg.

In another embodiment, the present invention provides a method of treating neuronal injuries, neuronal dysfunction and neurodegeneration, comprising the step of administering to a patient in need thereof a compositing comprising *Radix angelica sinensis* (DangGui), *Carthamus tinctorius* (Hong Hua), *Hirudo* (Shuizhi), *Polygonatum sibiricum* (Huangjing), and *Glycyrrhiza uralensis* (Gancao), wherein the g/kg body weight dosages can be increased up to 2.5 times if the body weight of the patient is less than 40 kg.

In one embodiment, the present invention provides a method of treating neuronal injuries, neuronal dysfunction and neurodegeneration, comprising the step of administering to a patient in need thereof a compositing comprising *Radix angelica sinensis* (DangGui), *Ligusticum chuanxiong* (ChuanXiong), *Hirudo* (ShuiZhi), *Polygonatum sibiricum* (HuangJing) *Glycyrrhiza uralensis* (Gancao) and *Astragalus membranaceus* (HuangQi), wherein the g/kg body weight dosages can be increased up to 2.5 times if the body weight of the patient is less than 40 kg.

In another embodiment, the present invention provides a method of treating neuronal injuries, neuronal dysfunction and neurodegeneration, comprising the step of administering to a patient in need thereof a compositing comprising *Radix angelica sinensis* (DangGui), *Ligusticum chuanxiong* (ChuanXiong), *Hirudo* (ShuiZhi), *Polygonatum sibiricum* (HuangJing), and one or more of the following: *Astragalus membranaceus* (HuangQi), *Lycium chinense mill* (GouQiZi), *Curculigo orchioides* (XianMao), *epimedium grandiflorum* (YinYangHuo), *plastrum testudinis* (ShengGuiBan), *Cornus officinalis* (ShanZhuYu), *Psoralea corylifolia* (BuGuZhi), *Leonurus heterophyllus* (YiMuCao), *Paeonia rubrae* (ChiShao), and *Glycyrrhiza uralensis* (Gancao).

In another embodiment, the present invention provides a method of treating neuronal injuries, neuronal dysfunction and neurodegeneration, comprising the step of administering to a patient in need thereof a compositing comprising *Radix angelica sinensis* (DangGui), *Carthamus tinctorius* (Hong Hua), *Hirudo* (ShuiZhi), *Polygonatum sibiricum* (HuangJing), and one or more of the following: *Astragalus membranaceus* (HuangQi), *Lycium chinense mill* (GouQiZi), *Curculigo orchioides* (XianMao), *epimedium grandiflorum* (YinYangHuo), *plastrum testudinis* (ShengGuiBan), *Cornus officinalis* (ShanZhuYu), *Psoralea corylifolia* (BuGuzhi), *Leonurus heterophyllus* (YiMuCao), *Paeonia rubrae* (ChiShao), and *Glycyrrhiza uralensis* (Gancao).

DETAILED DESCRIPTION OF THE INVENTION

According to the theory of Chinese medicine, neurodegenerative diseases belong to the category of Qi deficiency, "liver" and "kidney" weakness (Wei Zheng or Wei Syndrome). The terms "liver" and "kidney" in Chinese medicine do not merely include the liver and kidney in modern anatomical definition. The definition of "liver" includes liver, part of the CNS, autonomic nervous system, blood and visual systems; whereas the definition of "kidney" includes urinary system, reproductive system, part of the endocrine system and nervous system. BuNaoGao was designed to achieve its neuronal supporting effect through the nourishment of "liver" and "kidney", and the nourishment and mobilization and harmonization of "Qi" and "blood". Experimental studies in animal models had revealed its effect in improving blood circulation, reduction of blood viscosity and effect in immune regulation (5, 29). The approach of BNG to tackle neurodegenerative disease and neurodegeneration was through a mechanism of systemic nourishment and regulation.

Mental retardation and cerebral palsy: Our diagnosis of mental retardation also includes cerebral Palsy. According to the statistical data reported in America in 1973, the worldwide prevalence of mental retardation is 3% (mild type: 2.5%, moderate type. 0.5%); its prevalence in China is 0.5-2.7% (mild type) and 0.3-1% (severe type); the prevalence of cerebral palsy is 0.1-0.2% worldwide, and 0.1-0.4% (approximately 2 million in China). According the information released by American National Health Institute: more than 500,000 Americans have cerebral palsy (this information may also be considered as a reference for its global trend). The number of children and adults it affects has remained essentially unchanged or perhaps risen slightly over the past 30 years.

For paralysis or other disability caused by brain/spinal cord injury: There are currently 5.3 million Americans living with disability caused by head and spinal cord injury. Each year, at least 1.5 million people sustain brain injury (at a speed on every 21 seconds). This public health concern ranks as the leading cause of death and disability in children and young adults. Currently, prevention is the only known cure for brain injury. This statistics came from the information released by the Brain Injury Association, Inc. (Alexandria, Va., USA). This information may also be used as a reference for the worldwide trend of brain injury.

Dementia of all types: e.g. Alzheimer's disease (AD), the most common cause of dementia among people age 65 and older. It was estimated that up to 4 million people in America currently suffer with the disease, and the prevalence (the number of people with the disease at any one time) doubles every 5 years beyond age 65. Approximately 360,000 new cases are estimated to emerge each year and to increase as the population ages (According to the 2000 progress report on Alzheimer's disease from National Institute of Health of America). In China, over 5 millions people above the age 65 suffer from senile dementia (according to the information of a large-scale study by the Beijing Center of Gerontology, P.R. China, September 2002).

Motor neuron disease: Amyotrophic lateral sclerosis (ALS), often referred to as "Lou Gehrig's disease," is a fatal neurodegenerative disease and is the most common and the most severe form of motor neuron diseases. The vast majory of ALS patients dies within 2-5 years after diagnosis. Major clinical trials of the last 10 years has repeatedly revealed approximately 50% fatality or tracheotomy-free survival by the end of 15-18 months follow up (6-8). RILOZOLE is currently the only FDA approved drug for ALS and has proven in clinical trials to prolong ALS survival by approximately 3 months during the first 15 months of its use (6-9).

Treatment of all above conditions has been one of the biggest challenges to our biomedical field. Treatment regimes worldwide involve neuroprotectants and physical therapies, and these regimes have been expensive with only limited clinical benefits. No generally-accepted effective treatment is so far available. In recent years, there has been some progress in using Chinese Medicine for the treatment of the above diseases; however, their effectiveness has been limited due to big case-to-case variations and low reproducibility.

This invention was developed based on the inventor's over 30 years of clinical practice and academic exploration. The therapeutic scope of this invention touches the most sensitive and challenging areas of modern biomedical fields. Its efficacy in treating such a wide range of complicated diseases, its reproducibility, low toxicity and high social benefit will establish its position in the future biomedical field.

In one embodiment, 2 lozenges is a standard daily dose. For a person with body weight of 50-60 kg, the dosage range and the dosage present in 2 lozenges are listed below for the herbal ingredients: Radix angelica sinensis (DangGui) 0.82 g-3.3 g/Kg body weight, if 80 g/daily, 1.3-1.6 g/Kg; Ligusticum chuanxiong (ChuanXiong) 0.1-1.2 g/Kg body weight, if 20 g/daily, 0.33-0.4 g/Kg; Hirudo (ShuiZhi) 0.1-0.4 g/Kg body weight, if 10 g/daily, 0.16-0.2 g/Kg; Polygonatum sibiricum (HuangJing) 0.2-0.8 g/kg, if 20 g/daily, 0.33-0.4 g/Kg; Astragalus membranaceus (HuangQi) 0.315 g-1.2 g/Kg body weight, if 30 g/daily, 0.48-0.6 g/Kg; Lycium chinense mill (GouQizi) 0.1-1 g/Kg, if 12 g/daily, 0.24-0.24 g/Kg; Curculigo orchioides (XianMao) 0.1-1 g/Kg, if 9 g/daily, 0.15-0.18 g/Kg; epimedium grandiflorum (YinYangHuo) 0.1-1 g/Kg, if 9 g/daily, 0.15-0.18 g/Kg; plastrum testudinis (ShengGuiBan) 0.1-1 g/Kg, if 15 g/daily, 0.25-0.3 g/Kg; Cornus officinalis (ShanzhuYu) 0.1-1 g/Kg, if 10 g/daily, 0.16-0.2 g/Kg; Psoralea corylifolia (BuGuZhi) 0.1-1 g/Kg, if 12 g/daily, 0.24-0.24 g/Kg; Leonurus heterophyllus (YiMucao) 0.1-1 g/Kg, if 20 g/daily, 0.33-0.4 g/Kg; Paeonia rubrae (ChiShao) 0.1-1 g/Kg, if 20 g/daily, 0.33-0.4 g/Kg; Glycyrrhiza uralensis (Gancao) 0.06-0.21 g/Kg, if 6 g/daily, 0.1-0.12 g/Kg.

The present invention provides methods of treating neurodegenerative diseases or degenerative conditions. As an example, the following examples present data relating to treating patients with cerebral palsy, motor neuron disease/amyotrophic lateral sclerosis, spinal cerebella ataxia etc. Taking the present and prior disclosures as a whole, one of ordinary skill in the art would recognize that the present invention is not limited to treating only cerebral palsy, spinal cerebella ataxia (SCA), amyotrophic lateral sclerosis. The methods of treatment disclosed herein would be applicable to other neurodegenerative diseases. As used herein, "neurodegenerative diseases" include, but are not limited to, amyotrophic lateral sclerosis, Alzheimer disease, Olivopontocerebellar atrophy, and CNS inflammatory diseases such as myelitis, multiple sclerosis.

In one embodiment of the present invention, there is provided a method of treating neuronal injuries or neurodegenerative diseases, comprising the step of administering to a patient in need thereof a compositing comprising Radix angelica sinensis (DangGui) 0.82-3.3 g/kg body weight, Ligusticum chuanxiong (ChuanXiong) 0.1-1.2 g/kg body weight, Hirudo (Shuizhi) 0.1-0.4 g/kg body weight, and Polygonatum sibiricum (HuangJing) 0.2-0.8 g/kg body weight, wherein the g/kg body weight dosages can be increased up to 2.5 times if the body weight of the patient is less than 40 kg. In one embodiment, the composition is administered daily.

In another embodiment, the composition comprises Radix angelica sinensis (DangGui) 0.82-3.3 g/kg body weight, Carthamus tinctorius (Hong Hua) 0.1-1.2 g/kg body weight, Hirudo (Shuizhi) 0.1-0.4 g/kg body weight, and Polygonatum sibiricum (HuangJing) 0.2-0.8 g/kg body weight.

In another embodiment, the composition comprises Radix angelica sinensis (DangGui) 0.82-3.3 g/kg body weight,

*Ligusticum chuanxiong* (ChuanXiong) 0.1-1.2 g/kg body weight, *Hirudo* (ShuiZhi) 0.1-0.4 g/kg body weight, *Polygonatum sibiricum* (HuangJing) 0.2-0.8 g/kg body weight, and *Astragalus membranaceus* (HuangQi) 0.315-1.2 g/kg body weight.

In another embodiment, the composition comprises *Radix angelica sinensis* (DangGui) 0.82-3.3 g/kg body weight, *Carthamus tinctorius* (Hong Hua) 0.1-1.2 g/kg body weight, *Hirudo* (ShuiZhi) 0.1-0.4 g/kg body weight, *Polygonatum sibiricum* (HuangJing) 0.2-0.8 g/kg body weight, and *Astragalus membranaceus* (HuangQi) 0.315-1.2 g/kg body weight.

In another embodiment, the composition comprises *Radix angelica sinensis* (DangGui) 0.82-3.3 g/kg body weight, *Ligusticum chuanxiong* (ChuanXiong) 0.1-1.2 g/kg body weight, *Hirudo* (ShuiZhi) 0.1-0.4 g/kg body weight, *Polygonatum sibiricum* (HuangJing) 0.2-0.8 g/kg body weight, and *Glycyrrhiza uralensis* (Gancao) 0.06-0.21 g/kg body weight.

In another embodiment, the composition comprises *Radix angelica sinensis* (DangGui) 0.82-3.3 g/kg body weight, *Carthamus tinctorius* (Hong Hua) 0.1-1.2 g/kg body weight, *Hirudo* (ShuiZhi) 0.1-0.4 g/kg body weight, *Polygonatum sibiricum* (HuangJing) 0.2-0.8 g/kg body weight, and *Glycyrrhiza uralensis* (Gancao) 0.06-0.21 g/kg body weight.

In another embodiment, the composition comprises *Radix angelica sinensis* (DangGui) 0.82-3.3 g/kg body weight, *Ligusticum chuanxiong* (ChuanXiong) 0.1-1.2 g/kg body weight, *Hirudo* (ShuiZhi) 0.1-0.4 g/kg body weight, *Polygonatum sibiricum* (HuangJing) 0.2-0.8 g/kg body weight, *Astragalus membranaceus* (HuangQi) 0.315-1.2 g/kg body weight, and *Glycyrrhiza uralensis* (Gancao) 0.06-0.21 g/kg body weight. In one embodiment, the composition is administered daily. In another embodiment, the g/kg body weight dosages can be increased up to 2.5 times if the body weight of the patient is less than 40 kg.

In another embodiment, the composition comprises *Radix angelica sinensis* (DangGui) 0.82-3.3 g/kg body weight, *Ligusticum chuanxiong* (Chuanxiong) 0.1-1.2 g/kg body weight, *Hirudo* (Shuizhi) 0.1-0.4 g/kg body weight, *Polygonatum sibiricum* (HuangJing) 0.2-0.8 g/kg body weight, and one or more of the following: *Astragalus membranaceus* (HuangQi) 0.315 g-1.2 g/Kg body weight, *Lycium chinense mill* (GouQiZi) 0.1-1 g/Kg, *Curculigo orchioides* (XianMao) 0.1-1 g/Kg, *epimedium grandiflorum* (YinYangHuo) 0.1-1 g/Kg, *plastrum testudinis* (ShengGuiBan) 0.1-1 g/Kg, *Cornus officinalis* (ShanZhuYu) 0.1-1 g/Kg, *Psoralea corylifolia* (BuGuZhi) 0.1-1 g/Kg, *Leonurus heterophyllus* (YiMuCao) 0.1-1 g/Kg, *Paeonia rubrae* (ChiShao) 0.1-1 g/Kg, *Glycyrrhiza uralensis* (Gancao) 0.06-0.21 g/Kg.

In another embodiment, the composition comprises *Radix angelica sinensis* (DangGui) 0.82-3.3 g/kg body weight, *Carthamus tinctorius* (Hong Hua) 0.1-1.2 g/kg body weight, *Hirudo* (Shuizhi) 0.1-0.4 g/kg body weight, *Polygonatum sibiricum* (HuangJing) 0.2-0.8 g/kg body weight, and one or more of the following: *Astragalus membranaceus* (HuangQi) 0.315 g-1.2 g/Kg body weight, *Lycium chinense mill* (GouQiZi) 0.1-1 g/Kg, *Curculigo orchioides* (XianMao) 0.1-1 g/Kg, *epimedium grandiflorum* (YinYangHuo) 0.1-1 g/Kg, *plastrum testudinis* (ShengGuiBan) 0.1-1 g/Kg, *Cornus officinalis* (ShanzhuYu) 0.1-1 g/Kg, *Psoralea corylifolia* (BuGuZhi) 0.1-1 g/Kg, *Leonurus heterophyllus* (YiMuCao) 0.1-1 g/Kg, *Paeonia rubrae* (ChiShao) 0.1-1 g/Kg, *Glycyrrhiza uralensis* (Gancao) 0.06-0.21 g/Kg.

The invention being generally described, will be more readily understood by reference to the following examples which are included merely for purposes of illustration of certain aspects and embodiments of the present invention, and are not intended to limit the invention.

Content of Examples:

EXAMPLE 1 BuNaoGao in the treatment of children with mental retardation (a trial of 133 cases)

EXAMPLE 2 BuNaoGao in the treatment of children with cerebral palsy (a trial of 102 cases)

EXAMPLE 3 BuNaoGao in the treatment of paralysis as a result of head/spinal cord trauma (a trial of 66 cases)

EXAMPLE 4 BuNaoGao in the treatment of 23 patients of motor neuron disease

EXAMPLE 5 Treatment of patients in vegetative state (total four cases)

EXAMPLE 6 Treatment of Oliverpontocerebellar atrophy (Dejerine-Thomas type, 3 cases)

EXAMPLE 7 Treatment of hereditary cerebellar ataxia (3 cases)

EXAMPLE 8 Treatment of dementia

EXAMPLE 9 Treatment of 52 patients with sequel of apoplexy with Fe-Shou-Yi-Qi-Ho-Xieff" concoction EXAMPLE 10 Treatment of 50 patients of apoplexy combined with pseudo-bulbar palsy EXAMPLE 11 Treatment of encephalopathy EXAMPLE 12 Treatment of multiple sclerosis (MS)

EXAMPLE 13 Treatment of myelitis

EXAMPLE 14 Treatment of polyneuritis (polyneuropathy)

EXAMPLE 1

BuraoGao in the Treatment of Children with Mental Retardation (a Trial of 133 Cases) (10, 34)

1.1 General Information

This clinical trial was carried out between January 1989 and December 1992 at the Provincial Hospital of Chinese Medicine, Lanzhou, GanSu Province, P.R. China. The details are listed in table 1.1

TABLE 1.1

Treatment of children with mental retardation with BuNaoGao

|  | BuNaoGao group | Control group |
|---|---|---|
| Total cases | 75 | 58 |
| Male | 45 | 29 |
| Female | 30 | 29 |
| Range in Age | 4 months to 14 years | 1 year to 14 years |
|  | (5.8 years in average) | (5.9 years in average) |

TABLE 1.1-continued

Treatment of children with mental retardation with BuNaoGao

|  | BuNaoGao group | Control group |
|---|---|---|
| Age distribution: | | |
| 0-3 years | 28 | 13 |
| 4-6.5 years | 17 | 20 |
| 6.5 years and above | 30 | 25 |
| IQ (DQ for age < 3 years) | | |
| Marginal(IQ 70-79) | 6 | 5 |
| Mild(IQ 55-69) | 18 | 8 |
| Moderate(IQ 40-54) | 16 | 11 |
| Severe(IQ 25-39) | 20 | 9 |
| Most severe(IQ <24) | 15 | 25 |
| Brain CT scan | 26 tested | Not tested |
| Cortical atrophy: | 12 | |
| localized region of reduced densities | 5 | |
| localized region of high density | 1 | |
| Cerebellum atrophy | 1 | |
| Arachinoidal cyst | 2 | |
| Normal | 4 | |
| Electroencephalography (EEG) | 16 tested | Not tested |
| Mildly abnormal | 3 | |
| Moderately abnormal | 7 | |
| Highly abnormal | 6 | |
| Complications and concomitant diseases | | |
| Cerebral palsies | 69 | 24 |
| Major epilepsy | 17 | |
| Minor epilepsy | 2 | 1 |
| Myoclonic epilepsy | 6 | 2 |
| spontaneous movement | 6 | |
| Congenital heart disease | 1 | 1 |
| Congenital lip cleft | | 4 |
| Etiology | | not available |
| Premature birth | 15 | (because all cases were from the |
| Hypoxia during delivery | 23 | city's orphanage hospital) |
| Cesarean section | 3 | |
| Sequel of nuclear Jaundice | 3 | |
| Maternal history of severe infection | 3 | |
| Sign of embryonic abortion | 1 | |
| Unknown | 27 | 40 |

1.2 Treatment Strategy (Table 1.2)

TABLE 1.2

Treatment Strategy of BuNaoGao vs. control groups for mental retardation

|  | BuNao Gao group | Control |
|---|---|---|
|  | Oral intake of BuNaoGao alone | Oral intake of Nao-Fu-Kang* |
|  | No additional training | some also combined with acupuncture, or other medication, massage or planned exercises |
| Hospitalized | 23 cases | 58 cases (in the orphanage hospital) |
| Out-patients | 52 cases | |
| Dosage | <3 yr.: 0.5-1 cube/day | <5 yrs: 0.8-1.2 g/day |
|  | 3-6 yrs: 1 cube/day | 5-10 yrs: 1.8 g/day |
|  | >6 yrs: 1-2 cubes/day | >10 yrs: 2.4 g/day |
| Duration of treatment | | |
| 1 month | 24 cases | |
| 2 months | 25 cases | |
| 3 months | 14 cases | 58 cases |
| 4 months | 9 cases | |
| 6 months | 3 cases | |

*Nao-Fu-Kang is a commercially available herbal decoction commonly used for brain dysfunctions.

1.3 Criteria for Clinical Evaluation
Diagnostic Criteria for Mental Retardation

Intelligence obviously below average; IQ lower than average minus 2 SD (IQ <70, SD=15).

Deficits in age-appropriate behaviors.

At developmental stage (less than 18 years of age)

All children who entered the study satisfied the above three criteria.

Measurement of Intelligence

Gesell criteria: children of 4 weeks-3 years of age were evaluated with this criteria WPPSI criteria; 4-6.5 years of age WISC-R criteria: 6.5-16 years of age.

Criteria for Evaluating Therapeutic Effects (IQ was determined according to international standards)
Notable effect: increase of IQ >15 (including 15)
Improvement: increase of IQ 10-14 (including 10)
Effective: increase of IQ 5-9 (including 5)
No effect: increase of IQ <5

TABLE 1.4

Total effective rate of BuNaoGao and control groups for mental retardation of different severities

| Severity | Total effective rate | |
|---|---|---|
| | BuNaoGao | Control |
| total cases | 75 | 58 |
| Marginal | 5/6 (83%) | 4/5 (80%) |
| mild | 18/18 (100%) | 2/8 (25%) |
| moderate | 16/16 (100%) | 5/11 (45%) |
| severe | 16/20 (80%) | 5/9 (55%) |
| most severe | 11/15 (73%) | 1/25 (4%) |
| total | 66/75 (88%) | 17/58 (29.3%) |

Total effective rate includes the rates of notable effect, improvement and effective

TABLE 1.5

Analysis of BuNaoGao effect on mental retardation of Different severities (75 cases)

| | Notable effective | Improvement | effective | no effect | total effective |
|---|---|---|---|---|---|
| mild (IQ 55-69) | 6 | 7 | 5 | | 18/18 (100%) |
| moderate(IQ 40-54) | 7 | 3 | 6 | | 16/16 (100%) |
| severe(IQ 25-39) | 6 | 4 | 6 | 4 | 16/20 (80%) |
| most severe(IQ <24) | 5 | 2 | 4 | 4 | 11/15 (73%) |
| marginal (IQ 70-79) | 3 | 1 | 1 | 1 | 5/6 (83%) |
| % of total | 27 (36%) | 17 (22.7%) | 22 (29.3%) | 9 (12%) | 66 (88%) |

TABLE 1.6

Analysis of NaoFuKang (control group) for mental retardation of different severity (58 cases)

| | notable effective | Improvement | effective | no effect | total effective |
|---|---|---|---|---|---|
| mild (IQ 55-69) | 2 | | 1 | 6 | 2/8 (25%) |
| moderate (IQ 40-54) | 2 | 2 | 1 | 6 | 5/11 (45%) |
| severe (IQ 25-39) | 1 | 3 | 1 | 4 | 5/9 (55%) |
| most severe (IQ <24) | | | 1 | 24 | 1/25 (4%) |
| marginal (IQ 70-79) | 1 | 2 | 1 | 1 | 4/5 (80%) |
| % of Total | 6 (10.3%) | 17 (12.1%) | 4 (7%) | 41 (70.7%) | 17 (29.3%) |

1.4 Results

TABLE 1.3

Therapeutic efficacy of BuNaoGao for children with mental retardation

| Effect | BuNaoGao (%) | Control (%) |
|---|---|---|
| Total cases | 75 | 58 |
| Notable effect | 27 (36%) | 6 (10%) |
| Improvement | 17 (23%) | 7 (12%) |
| Effective | 22 (29%) | 4 (7%) |
| No effect | 9 (12%) | 41 (71%) |
| Total effective | 66 (88%) | 17 (29%) |

1.5 Clinical Follow-up 50 out of 75 cases in the BuNaoGao group were followed up for a period of 3 months to 4 years, the intelligence of all patients were found in stable conditions or had continued improvement. No single case of deterioration was reported during this period.

1.6 Conclusion and Remarks

For the treatment of children mental retardation using BuNaoGao: The rate for notable effective is significantly higher in BuNaoGao group (36%) than that of the control group (10%). $P<0.001$. The total effective rate of the BuNaoGao group (88%) is significantly higher than that of the control group (29%). $P<0.001$. For mild type, the total effective rate of the BuNaoGao group (100%) is significantly higher than that of the control group (25%). P<0.001. For moderate type, the total effective rate of the BuNaoGao group (100%) is significantly higher than that of the control group (45%). P<0.01. For severe and most severe types, the total effective rate of the BuNaoGao group (77.1%) is significantly higher than that of the control group (18%). P<0.01. Therefore BuNaoGao is found to have significant therapeutic effect on children mental retardation.

EXAMPLE 2

BuNaoGao in the Treatment of Children with Cerebral Palsy (a Trial of 102 Cases) (11, 33)

2.1 General Information

This clinical trial was carried out between January 1989 and December 1992 by the Provincial Hospital of Chinese Medicine, Lanzhou, GanSu Province. The details are listed in Table 2.1.

TABLE 2.1

BuNaoGao for children with cerebral palsy

| | BuNaoGao group | Control group |
|---|---|---|
| No. of Cases | 78 | 24 |
| Male | 47 | 14 |
| Female | 31 | 10 |
| Range in Age | 4 months to 13 years (5.9 years in average) | 1 year to 9.5 years (4.1 years in average) |
| Age distribution: | | |
| 0-3 years | 34 | 7 |
| 4-6.5 years | 21 | 11 |
| 6.5 years and above | 23 | 6 |
| Severity by muscle strength | | |
| Mild($III^+$-V) | 9 (11.5%) | 11 (45.8%) |
| Moderate ($II^+$-III) | 42 (53.8%) | 10 (41.7%) |
| Severe ($I^+$-II) | 24 (30.8%) | 3 (12.5%) |
| Most severe (0-I) | 3 (3.85%) | 0 |
| Type of cerebral palsies | | |
| Spastic type | 59 | 11 |
| Athetosis | 1 | 1 |
| Rigidity | 1 | 1 |
| Ataxic type | 10 | |
| Tremor | 2 | |
| dystonic type | 5 | 11 |
| Severity of paralysis | | |
| Quadriplegia | 64 | 17 |
| Paraplegia | 3 | 3 |
| Hemiplegia | 8 | 3 |
| Monoplegia | 1 | 1 |
| Brain CT scan | 29 tested | not tested |
| Cortical atrophy: | 12 | |
| localized region of reduced densities | 9 | |
| localized region of high density | 1 | |
| Cerebellum atrophy | 1 | |
| Arachinoidal cyst | 2 | |
| Normal | 3 | |
| Electroencephalography (EEG) | 21 tested | not tested |
| Slightly abnormal | 4 | |
| Moderately abnormal | 11 | |
| Highly abnormal | 6 | |
| Complications & concomitant diseases | | |
| Cerebral feeblemindedness | 68 | 24 |
| Major epilepsies | 20 | |
| pyknolepsy | 2 | 1 |
| Myoclonic epilepsy | 4 | |
| Spontaneous movement | 3 | |
| Congenital heart disease | 1 | 1 |
| Etiology | | not available* (because all cases were from the city's orphanage hospital) |
| Premature birth | 12 | |
| Hypoxia during delivery | 23 | |
| Cesarean section | 3 | |
| Sequel of nuclear jaundice | 3 | |
| Maternal history of severe infections | 5 | |
| Unknown | 30 | |

2.2. Treatment Strategy (Table 2.2)

TABLE 2.2

Treatment Strategy for BuNaoGao vs. control groups for cerebral palsy

|  | BuNaoGao group | Control |
|---|---|---|
|  | Oral intake of BuNaoGao alone No additional training or other medications | Oral intake of Nao-Fu-Kang* some also combined with planned exercise, acupuncture, massage |
| Total Cases | 78 | 24 |
| Hospitalized | 23 | 24 (in the Orphanage hospital) |
| Out-patients | 55 |  |
| Dosage | <3 yrs, 0.5-1 cube/day<br>3-6 yrs: 1 cube/day<br>>6 yrs: 1-2 cubes/day | <5 yrs, 0.8-1.2 g/day<br>5-10 yrs: 1.8 g/day<br>>10 yrs: 2.4 g/day |
| Duration of treatment |  |  |
| 1 month | 24 |  |
| 2 months | 32 |  |
| 3 months | 20 | 24 |
| 4 months | 2 |  |

*Nao-Fu-Kong is a commercially available herbal decoction commonly used for brain dysfunction 2.3 Criteria for Clinical Evaluation (the Internationally used Six Grade Criteria)

Cured: movement become normal, muscle strength reach grade V

Notable effect: movement function significantly improved, muscle strength improved over 2 grade.

Effective: movement function improved, muscle strength improved over 1 grade.

No effect: no improvement of movement function, muscle strength improved less than 1 grade.

2.4. Results (Tables 2.3-2.6)

TABLE 2.3

Therapeutic efficacy of BuNaoGao for children with cerebral palsy

| Effect | BuNaoGao (%) | Control (%) |
|---|---|---|
| total Case | 78 | 24 |
| Cured | 7 (9%) | 0 |
| Notable effect | 21 (26.9%) | 1 (4.2%) |
| Effective | 46 (59%) | 4 (16.7%) |
| No effect | 4 (5.1%) | 19 (79.2%) |
| Total effective | 74 (98.9%) | 5 (20.8%) |

TABLE 2.4

Total effective rate of BuNaoGao and control for cerebral palsy of different severities

|  | Total effective rate | |
|---|---|---|
| Severity | BuNaoGao | Control |
| total cases | 78 | 24 |
| mild | 8/9 (88.9%) | 4/11 (36.4%) |
| moderate | 39/42 (92.9%) | 1/10 (10%) |
| severe | 24/24 (100%) | 0/3 (0) |
| most severe | 3/3 (100%) | 0 (0) |
| total | 74/78 (94.9%) | 5/24 (20.8%) |

Total effective rate includes the rate of cured, notable effect and effective.

TABLE 2.5

Analysis of BuNaoGao effect for cerebral palsy of different severities (78 cases)

|  | Cured | Notable effect | Effective | No effect | Total effective(%) |
|---|---|---|---|---|---|
| mild | 2 |  | 6 | 1 | 8/9 (88.9%) |
| moderate | 5 | 9 | 25 | 3 | 39/42 (92.9%) |
| severe |  | 10 |  | 14 | 24/24 (100%) |
| most severe |  | 2 |  | 1 | 3/3 (100%) |
| % of total | 7/78 (8.97%) | 21/78 (26.9%) | 46/78 (59%) | 4/78 (5.1%) | 74/78 (94.9%) |

TABLE 2.6

Analysis of Nao-Fu-Kang effect (control) for cerebral palsy of different severities (24 cases)

|  | cured | notable effect | effective | no effect | total effective(%) |
|---|---|---|---|---|---|
| Mild |  | 1 | 3 | 7 | 4/11(36.4%) |
| moderate |  |  | 1 | 9 | 1/10 (10%) |
| severe |  |  |  | 3 | 0/3 (0) |
| most severe |  |  |  |  | 0 (0) |
| % of total | 0 | 1/24 (4.17%) | 4/24 (16.7) | 19/24 (79.2%) | 5/24 (20.8%) |

2.5 Clinical Follow-Up 60 of 78 cases in the BuNaoGao group were followed up for a period of 3 months to 4 years, all patients were found in stable conditions or had shown continued improvement. No single case of deterioration was reported.

2.6 Conclusion and Remarks

For the treatment of children cerebral palsy using BuNaoGao: The rate for notable effective plus cured is significantly higher in BuNaoGao group (35.9%) than that of the control group (4.2%), P<0.005. The total effective rate of the BuNaoGao group (98.9%) is significantly higher than that of the control group (20.8%), P<0.005. For mild type of cerebral palsy, the total effective rate of the BuNaoGao group (88.9%) is significantly higher than that of the control group (36.4%), P<0.01. For moderate type of cerebral palsy, the total effective rate of the BuNaoGao group (92.9%) is significantly higher than that of the control group (10%), P<0.005. For severe type of cerebral palsy, all of the 24 cases in BuNaoGao group (100%) showed effective results, and none of the 3 cases in the control group showed any effect. For most severe type of cerebral palsy, all three cases treated by BuNaoGao gained effective results, and no patient of this severity was included in the control group. Therefore BuNaoGao was found to have significant therapeutic effect on cerebral palsy.

EXAMPLE 3

BuNaoGao in the Treatment of Paralysis as a Result of Head/Spinal Cord Trauma (a Trial of 66 cases) (1, 30)

3.1 General Information

This clinical trial was carried out between January, 1989 to December, 1992 by the Provincial Hospital of Chinese Medicine, Lanzhou, GanSu Province. The details are listed in Table 3.1.

TABLE 3.1

General information of patients with paralysis resulting from head/spinal cord trauma in BuNaoGao group and control group.

|  | BuNaoGao group | Control group |
| --- | --- | --- |
| Total cases | 46 | 20 |
| Male: | 34 | 15 |
| Female: | 12 | 5 |
| In-patients | 34 | 20 |
| Outpatients | 12 |  |
| Range in Age | 1.5 to 71 yrs (average 29 yrs) | 8 to 50 yrs (average 32 yrs) |
| 0-9 yrs | 6 | 1 |
| 10-17 yrs | 2 | 5 |
| 18-29 yrs | 16 | 0 |
| 30-39 yrs | 8 | 6 |
| 40-59 yrs | 12 | 8 |
| >60 yrs | 2 | 0 |
| Disease Severity |  |  |
| Mild (III$^+$-V$^-$)* | 12 | 8 |
| Moderate (II$^+$-III) | 17 | 4 |
| Severe (I$^+$-II) | 10 | 3 |
| Very severe (0-I) | 7 | 5 |
| Duration of illness |  |  |
| <1 month | 3 | 0 |
| 1-3 months | 8 | 4 |
| 3-6 months | 5 | 2 |
| 6-12 months | 10 | 3 |
| 1-3 years | 13 | 11 |
| 3-5 years | 5 | 0 |
| 5-10 years | 1 |  |
| 15 years | 1 |  |
| Cause of injuries |  |  |
| Car accident | 20 | 2 |
| Bicycle accident | 3 |  |
| Motorcycle accident | 1 | 2 |
| Fall from high places | 4 | 1 |
| Fall from flat ground | 5 |  |
| Manslaughter | 9 | 1 |
| Heavy object struck | 2 | 14 |
| surgery | 1 |  |

TABLE 3.1-continued

General information of patients with paralysis resulting from head/spinal cord trauma in BuNaoGao group and control group.

|  | BuNaoGao group | Control group |
| --- | --- | --- |
| Complications |  |  |
| Headache | 33 | 9 |
| Dizziness | 31 | 8 |
| Aphasia | 11 | 2 |
| Dysphasia | 15 | 7 |
| Dysphagia | 7 | 3 |
| Sleepiness | 5 | 2 |
| Slow responsiveness | 11 | 3 |
| mentally retarded | 12 |  |
| Decerebral rigidity | 4 |  |
| vegetative states | 3 |  |
| lack of bladder and bowl control | 13 | 5 |
| optic nerve atrophy | 1 | 3 |
| blurred vision | 3 |  |
| facial nerve paralysis | 3 | 1 |
| epilepsy | 7 | 3 |
| multiple cranial nerve injury | 1 | 1 |
| Brain CT scan | 33 tested | 7 tested |
| normal | 7 | 1 |
| localized region of reduced density | 12 | 4 |
| localized region of high density | 3 |  |
| Intracranial hematoma | 3 | 6 |
| Epidural hematoma | 4 | 1 |
| Subdural hematoma | 1 |  |
| Subdural fluid | 3 |  |
| Hydrocephalus | 2 |  |
| Brain atrophy | 3 |  |
| Brain infarct | 2 |  |
| Skull fracture | 14 |  |
| Electroencephalography (EEG) | 40 tested | 6 tested |
| Normal: | 5 |  |
| Slightly abnormal: | 14 | 1 |
| Moderately abnormal: | 16 | 1 |
| Severely abnormal: | 5 | 4 |
| Diagnosis |  |  |
| Brain laceration | 29 | 12 |
| Brain laceration combined with skull base fracture | 1 |  |
| Intracranial hematoma | 8 | 7 |
| Chronic intracranial hematoma | 1 |  |
| Epidural hematoma | 4 |  |
| Subdural hematoma |  | 1 |
| Brain stem injury (vegetative state) | 3 |  |
| Lingual diagnosis |  |  |
| Substance of tongue |  |  |
| pinkish (Dan Hong) | 8 | 5 |
| red (Hong) | 16 | 9 |
| dark red (Hong An) | 8 | 3 |
| plain (Dan) | 12 | 2 |
| dark plain (Dan An) | 2 | 1 |
| Tongue coating |  |  |
| Thin white coating (Bo Bai) | 8 | 12 |
| white coating (Bai) | 22 | 2 |
| white glossy coating (Bai Ni) | 5 | 2 |
| yellow coating (Huang) | 7 | 3 |
| yellow glossy coating (Huang Ni) | 3 | 3 |
| little coating (shao tai) | 1 |  |
| Pulse |  |  |
| fine pulse (Xi Mai) | 24 |  |
| stringy pulse (Xuan Mai) | 13 | 8 |
| stringy large pulse (Xuan Da Mai) | 1 |  |
| stringy fine pulse (Xuan Xi Mai) |  | 3 |
| rapid pulse (Shu Mai) | 1 |  |
| Slippery pulse (Hua Mai) | 5 |  |
| Deep slow pulse (Chen Huan Mai) | 2 |  |
| Deep stringy pulse (Chen Xuan Mai) | 2 |  |
| Fine rapid pulse (Xi Mai) | 1 |  |
| Deep fine pulse (Chen Xi Mai) | 6 |  |

TABLE 3.2

Treatment Strategy for BuNaoGao & control groups for paralysis by head/spinal cord trauma

|  | BuNaoGao | Control |
|---|---|---|
|  | Oral intake of BuNaoGao alone No additional training or other medications | Combined treatment of Chinese & Western medicines, acupuncture, physical therapy |
| Total cases | 46 | 20 |
| Hospitalized | 34 | 20 |
| Out-patients | 12 |  |
| Dosage | 2 cubes/day |  |
| Duration of treatment |  |  |
| 1 month | 10 | 4 |
| 2 months | 16 | 3 |
| 3 months | 6 | 2 |
| >3 months | 14 | 11 |

3.2 Criteria for Clinical Evaluation (The Internationally Used Six-Grade Criteria).

Cured: movement became normal, muscle strength reached to grade V

Notable effect: muscle strength improved over 2 grade.

Effective: muscle strength improved over 1 grade.

No effect: muscle strength improved less than 1 grade.

3.3 Results

TABLE 3.3

Therapeutic efficacy of BuNaoGao for paralysis after head trauma

| Effect | BuNaoGao (%) | Control (%) |
|---|---|---|
| Total | 46 | 20 |
| Cured | 7 (15%) | 0 |
| Notable | 15 (33%) | 3 (15%) |
| Effective | 21 (46%) | 5 (25%) |
| No effect | 3 (6%) | 12 (60%) |
| Total effective | 43 (93%) | 8 (40%) |

TABLE 3.4

Effective rate of BuNaoGao and control group for paralysis of different severities

| | Total effective rate | |
|---|---|---|
| Severity | BuNaoGao | Control |
| Total | 46 | 20 |
| Mild($III^+$-$V^-$) | 10/12 (83%) | 3/8 (37.5%) |
| moderate($II^+$-III) | 16/17 (94.1%) | 2/4 (50%) |
| severe($I^+$-II) | 10/10 (100%) | 3/3 (100%) |
| most severe(0-I) | 7/7 (100%) | 0/5 (0) |
| Total effective | 43/46 (93.4%) | 8/20 (40%) |

TABLE 3.5

Analysis of BuNaoGao effect on paralysis of different severities (46 cases)

| | Cured | Notable effect | Effective | No effect | Total effective (%) |
|---|---|---|---|---|---|
| mild ($III^+$-$V^-$) | 6 |  | 4 | 2 | 10/12 (83.3%) |
| moderate | | 2 | 14 | 1 | 16/17 (94.1%) |
| ($II^+$-III) | | | | | |
| severe ($I^+$-II) | | 7 | 3 | | 10/10 (100%) |
| most severe (0-I) | 1 | 6 | | | 7/7 (100%) |
| % of Total | 7 (15.2%) | 15 (32.6%) | 21 (45.6%) | 3 (6.5%) | 43/46 (93.4%) |

TABLE 3.6

Analysis of the control group effect on paralysis of different severities (20 cases)

| | Cured | Notable effect | Effective | No effect | Total effective (%) |
|---|---|---|---|---|---|
| Mild ($III^+$-$V^-$) | | | 3 | 5 | 3/8 (37.5%) |
| Moderate ($II^+$-III) | | | 2 | 2 | 2/4 (50%) |
| severe ($I^+$-II) | | 3 | | | 3/3 (100%) |
| most severe (0-I) | | | | 5 | 0/5 (0) |
| % of Total | 0 | 3 (15%) | 5 (25%) | 12 (60%) | 8/20 (40%) |

3. 4. Conclusion and Remarks

For the treatment of paralysis after head/spinal cord trauma using BuNaoGao: The total effective rate of the BuNaoGao group (93%) is significantly higher than that of the control group (40%). P<0.005. The rate for notable effective plus cured is significantly higher in BuNaoGao group (47.8%) than that of the control group (15%). P<0.025. Therapeutic efficacy for other neuropsychological symptoms: Three patients in vegetative state regained consciousness, and one patient can move around easily. With the exception of no improvement for two cases of aphasia, and two cases of dysphasia, all other symptoms are either cured or notably improved. BuNaoGao has clearly demonstrated potent therapeutic efficacy for paralysis caused by head/spinal cord trauma.

EXAMPLE 4

BuNaoGao in the Treatment of 23 Patients with Motor Neuron Disease (2, 35)

4.1. General Information

This clinical trial was carried out between January, 1989 and December, 1992 by the Provincial Hospital of Chinese Medicine, Lanzhou, GanSu Province.

Total cases: 23 cases 20 cases hospitalized, 3 cases outpatient

Age: Range 24 to 68 years of age (average 44 years)

4 cases (20-29 years of age), 2 cases (30-39 years of age), 7 cases (40-49 years of age), 8 cases (50-59 years of age), 2 cases (over 60 years of age).

Stage of Progression:
   2 cases mild (muscle strength grade III$^+$~V$^{31}$, no bulbar syndromes).
   8 cases moderate (muscle strength grade II$^+$~III, no bulbar syndromes.
   13 cases Severe (muscle strength grade 0~II or with bulbar syndromes.
   11 out of the 23 patients had bulbar syndromes. Most cases had been treated elsewhere before being included in the BuNaoGao trial.

Duration of Illness:
   4 cases<1 year
   9 cases 1-3 years
   4 cases 3-5 years
   3 cases 5-7 years
   2 cases 7-10 years,
   1 case>10 years.
   EMG: 20 cases were tested for EMG, and all suggested damage of neuronal origin.

Clinical Diagnosis:
   Amyotrophic lateral sclerosis: 13 cases
   7 cases without bulbar syndromes,
   6 cases with bulbar syndromes.
   Primary lateral sclerosis: 8 cases
   4 cases without bulbar syndromes,
   4 cases with bulbar syndromes.

Progressive muscular atrophy: 2 cases
   1 case without bulbar syndromes,
   1 case with bulbar syndromes.

Complications and Concomitant Conditions:
   3 cases with coronary heart disease,
   1 case with cerebral infarct,
   1 case with hepatitis B,
   4 cases with lung infection,
   1 case with respiratory palsy.
   ECG: 20 cases tested
   10 cases normal,
   4 cases with insufficient coronary blood supply,
   3 cases right heart enlargement
   1 case incomplete right-bundle block
   2 cases incomplete left-bundle block (frontal branch)
   Lingual diagnosis: (a diagnostic technique by observing the texture, color and moisture of the coating and the substance of the tongue)
   Substance of tongue:
   4 cases pinkish (Dan Hong);
   4 cases red (Hong);
   3 cases dark red (Hong An);
   6 cases dark plain (Dan An);
   6 cases plain (Dan);
   Tongue coating:
   16 cases white coating (Bai);
   1 case white glossy coating(Bai Ni);
   3 cases yellow coating (Huang);
   3 cases yellow glossy coating (Huang Ni).
   Pulse:
   16 cases fine pulse (Xi Mai)
   6 cases stringy pulse (Xuan Mai)
   1 case rapid pulse (Shu Mai)

4.2 Treatment Strategy
   BuNaoGao alone, taken orally 2 cubes/day
   7 cases—finished 30-day treatment
   5 cases—finished 60-day treatment
   4 cases—finished 90-day treatment
   7 cases—finished over 90-day treatment
   Due to the often fast-deteriorating nature of this disease and the ethical issues involved, no control group was set up for this study.

4.3 Criteria for Therapeutic Efficacy
   Due to the already well-established course of development for this disease, efficacy of the treatment is evaluated based on patients' pre-treatment conditions and the trend of deterioration.
   Clinically cured: disappearance of bulbar palsy, muscle strength improved to grade V.
   Notable effect: bulbar palsy significantly improved, muscle strength improved more than 2 grade.
   Effective: bulbar palsy improved, muscle strength improved more than 1 grade.
   No effect: bulbar palsy continue to exist, no improvement of muscle strength or improvement was less than 1 grade.
   Deteriorated: continuous deterioration of symptoms or death.

4.4 Results (Table 4.1)

TABLE 4.1

Therapeutic efficacy of BuNaoGao on motor-neuron diseases (23 cases)

|  | mild | moderate | severe |
|---|---|---|---|
| Total | 2 | 8 | 13 |
| cured |  | 1 |  |
| notable |  | 3 | 2 |
| effective | 2 | 3 | 8 |
| no effect |  | 1 | 2 |
| deteriorated |  |  | 1 |
| Total effective | 2/2 | 7/8 | 10/13 |

In this study, to the one ALS patient who died during the period of our evaluation, a 3-cubes/day dosage was used at the late stage in an effort to get his conditions under control, and some positive effects were observed even at the very late stage. This patient had been repeatedly treated by BuNaoCao during the 8-year period after the initial diagnosis, and he made improvements in prior episodes of BuNaoGao treatment. This patient belonged to the fast-deteriorating type. According to the inventor's experience, if untreated, this patient's natural course of disease may be 2-3 years. This patient appeared to have a family history of similar disorders.

In our experience, the 2-cubes/day dosage was adequate for most patients. When this dosage failed to get the condition under control, a 3-cubes/day dosage (1.5 times of the daily dosage) was used. As soon as the patient's condition was stabilized, the dosage was reduced to the usual 2-cubes/day dosage. Although no side effect had been seen with the 3-cubes/day dosage, patients were not advised to go on this high dosage unnecessarily.

4.5. Strategy for Longer-Term Treatment
   After the clinical evaluation during the stated periods, patients were discharged from the hospital when considered clinically safe. Most patients took 0.5-1 year's supply of BuNaoGao for continued treatment as outpatients.
   Every three-month treatment was considered as one cycle. Patients were advised to take a one-week break after each three-month cycle to avoid any potential side effects (on the condition that the disease was in a reasonably stable condition). After taking BuNaoGao for 3-6 months, if the disease showed no sign of comeback after BuNaoGao was stopped, these patients could stop taking BuNaoGao. However, patients were advised to be back on BuNaoGao immediately as soon as there was a concern (or any signs) suggesting a comeback of the disease.

Some patients remained stable for many years without continuously taking BuNaoGao; some patients had to be back on BuNaoGao for more cycles of treatment when the problems resurfaced. Due to the lack of an effective follow-up mechanism for this disease in our system, long-term follow-up data is not yet available, and this information may become available at a later date.

All patients were advised to avoid stressful situations of all kinds, physical exercise was not recommended for muscle strengthening in this disease.

4.6. Examples of Typical Cases

In addition to the above-summarized report, the following cases reports gave more detailed description of changes in patients with this type of disease.

Case #1 (Amyotrophic Lateral Sclerosis) (12)

Patient: A 50-year-old female (Administration number #69834). Progressive upper limbs weakness for approximately 9 months, was admitted to the hospital on Sept. 18, 1992 with the diagnosis of amyotrophic lateral sclerosis (ALS). The patient begun feeling upper limb weakness without any known reason, later experienced difficulty of raising arms and were unable to unbutton her clothes, and also felt weakness on both lower limbs. EMG (done at other hospital): muscle abnormality of neuronal origin, all nerves tested showed abnormalities of different extents; Diagnosis by other hospital: amyotrophic lateral sclerosis (ALS); After failed all other regular treatments of both Chinese and Western Medicines, and with a progressively worsening condition, the patient was admitted to our hospital. Upon hospitalization: the patient showed weakness of all four limbs, could not raise her upper limbs above shoulder, both hands could not do gripping and stretching, could not unbutton her clothes, difficulty of lifting her feet while walking with a feeling of rigidity, could only go up and down stairs by holding onto railing, could see muscle jumping all over her body. Tongue: pink red, with a thin white coat, fine pulse. Physical exam: Cranial nerves (normal); obvious atrophy of thenar muscles interosseous muscles and forearm muscles and fasciculation, and muscle strength $III^-$; no muscle atrophy in the lower limbs, and muscle strength $III^+$; muscle tone of four limbs (low); reflexs of ankle-jerk, Biceps-jerk, Triceps-jerk and Knee-jerk are all hyperactive; Unable to induce pathological reflexes. No abnormalities of bladder control and bowel movement; No abnormality in sensory. Diagnosis according to Western Medicine: amyotrophic lateral sclerosis (ALS). Diagnosis according to Chinese Medicine: Wei Zheng (belong to insufficiencies of liver and kidney, and insufficiencies of Qi and blood), therefore the treatment strategy require nourishment of liver, kidney, Qi and blood. Treatment given: BuNaoGao (two cubes/day) alone. Two weeks after BuNaoGao; increased muscle strength in four limbs, could raise upper limbs above head but could not stretch straight; reduced rigidity in the lower limbs and reduced muscle jumping in whole body. One month after BuNaoGao; could raise upper limbs above should and could stretch straight, could do up and down stairs more freely than before. Two months after BuNaoGao, all five fingers of both hands could stretch out and could unbutton clothes, could go up and down stairs easily, muscle strength $III^+$-$V^-$. After being considered to have made an notable improvement, the patient was discharged from the hospital.

Case #2 (Amyotrophic Lateral Sclerosis) (13)

Patient: A 25-year-old male (Administration number #73819). Weakness of four limbs for approximately one year, was admitted to the hospital on Aug. 7, 1993 with the diagnosis of amyotrophic lateral sclerosis (ALS). Upon hospitalization; the patient showed weakness of all four limbs, weak gripping (only 5 Kg), obvious muscle atrophy of four limbs and both hands, twitching of both both upper limbs, unsteady walking (could only manage 100 meters), difficulty of walking up and down stairs. Tongue: red, with white coat, fine pulse. Physical exam: Lung and heart (−), muscle strength of four limbs (grade III), muscle tone (normal), tendon reflex (hyperactive), Babinski sign on both sides (+), Hoffmann sign on both sides (+); EMG: injury of neuronal origin. Diagnosis according to Chinese Medicine: Wei Zheng (liver and kidney weakness); Diagnosis according to Western Medicine: amyotrophic lateral sclerosis (ALS). Treatment strategy: BuNaoGao (two cubes/day) alone. 20 days after BuNaoGao: slightly enriched muscle volume, walking more steadily than before, gripping of both hands increased from 5 Kg to 20 Kg, could walk by himself for 2-3 hours, could walk up and down stairs by himself rather easily, muscle strength of four limbs V-. After one-month treatment with BuNaoGao, significant improvement was observed and the patient was discharged.

Case #3 (Primary Lateral Sclerosis) (14)

Patient: A 51-year-old male with a 6-month history of weakness in four limbs and lower limb rigidity, and was diagnosed by neurologists of other hospitals as "lateral sclerosis". His symptoms worsened continuously despite all the treatments with both Chinese and Western medicines before being admitted to our hospital.

Diagnosis: Primary Lateral Sclerosis.

After treatment with a decoction modified from "Fu Shou San", the patient showed improved in muscle strength after 15 day's treatment, and can climb stairs without the need for aid (still had difficulty of going downstairs) after 20 day's treatment; he can walk freely (still with some weakness) after 35 day's treatment. After 80 day's treatment, the patient's muscle strength reach grade V (still slight weakness), could walk up and down stairs easily and had normal gait. His pathological reflexes disappeared, and physiological reflexes of four limbs were only slightly active.

This patient was treated with a decoction when the cube form of BuNaoGao (or the consensus formulation) was not yet invented, nevertheless this report reflected one of the early attempts by the inventor to define a therapeutic rule (or consensus formulation) for treating this type of disease.

4.7. Side Effects

Due to the rather rapidly deteriorating nature of motor neuron disease (particularly ALS), and the potential of a long-term repeated use of BuNaoGao for these patients, the following advice and precautions were given to patients: This formulation was designed to be used alone without anticipating further combination with other drugs or supplements without proper medical supervision. Furthermore, people with certain medical conditions may put themselves at risk by using this formulation: i.e. (a) people with hypertension with blood pressure above 150/90 mmHg may put themselves at risk by taking this formulation without first lowing their blood pressure to a clinically safe level; (b) people with problems with blood clotting (i.e. bleeding tendency) may put themselves at risk by taking this formulation due to the anti-coagulating effect of this formulation; (c) Women in pregnancy or lactation should not use this formulation.

The only known side-effect of this formulation in people with suitable medical conditions (according to the experience of more than 25 years) has been an increased bowel movement, a problem which will usually resolve by itself within the first one or two weeks' usage. Despite the anti-coagulation effect of the formulation, no bleeding tendency has so far been reported from our long-term experience. For longer-term usage, a one-week break after every three-months usage is recommended.

4.8 Conclusion

Most patients treated by BuNaoGao has failed conventional treatment elsewhere (both Chinese and Western medicines). BuNaoGao has shown to be effective for treating motor-neuron disease with a total effective rate of 82.61% during the period of our evaluation. During the follow-up period (though incomplete), some patients (including some ALS patients) remained stable for many years without continuously using BuNaoGao; Some other ALS patients experienced the comeback of the disease several times. In every occasion of the disease comeback, BuNaoGao had demonstrated its beneficial effect on slowing the disease progression. BuNaoGao has demonstrated a significant effect on slowing-down the progression of ALS and other forms of motor neuron diseases. Given the severe nature of the disease, continuous treatment under monitoring and early treatment is always highly recommended.

During the period of 2000-2007, BuNaoGao for ALS/MND management was explored on a larger scale in the western patients' population. Further information will be entered upon completion of this work or upon request.

EXAMPLE 5

Treatment of Patients in Vegetative State (Total Four Cases) (15,16)

Patient #1: An 18-year-old female, in a vegetative state for 10 months after initial head injury. After taking BuNaoGao (cube form) for 10 days, she appeared to be in a slightly conscious state and to be able to recognize people; on the 15$^{th}$ day, she was able to swallow food and feeding tube was removed; on 20$^{th}$ day, she was able to speak simple words and could recognize her parents, had some improvement on limb muscle strength (strength grade I); Two months after BuNaoGao, she showed continued improvement on consciousness and intelligence (could remember her date of birth, could call out the names of her classmate, could tell Dr. Xia that "Uncle Xia, I have lost my intelligence", could translate a few English words into Chinese), etc (note: this is only a partial translation) (16).

Patient #2: A 17-year-old female, in a vegetative state for 6 month after brain surgery. Diagnosis: Injury to cerebral and brain stem, coma, de-celebral rigidity (vegetative state). 14 days after taking BuNaoGao, she appeared to be in a slightly conscious state and to be able to recognize objects; 20 days after taking BuNaoGao, she could answer yes or no with her eyes and could express her emotions; one month after taking BuNaoGao, she regained a clear consciousness, muscle strength had improved with decreased rigidity; Two month after taking BuNaoGao, she could speak simple sentences; 70 days after taking BuNaoGao, she could sit up, turn her neck, muscle strength in four limbs (I-III), reduced muscle rigidity, and decerebrate rigidity was relieved. (Note: this is only a partial translation) (16).

Patient #3: An 8-year-old girl with a three-month history of paralysis and in vegetative state (post encephalitis). Three month prior, the patient was admitted to a hospital due to a high fever followed by a state of coma, and was diagnosed as type B encephalitis. Both CT and EEG revealed widespread damage and abnormality of cerebral cortex. After various emergency treatments, she remained to be in a state of dementia, quadriplegia, tracheotomy, opisthotonus, a vegetative state. After treatment with a decoction of Chinese Medicine (with constant modifications) for 15 days, she started to show clinical improvements; after 30 days treatment, she made significant improvements (i.e. could speak simple words, muscle strength improved, etc.); After 60 days treatment, her intelligence was close to normal, could speak normally. After another month of treatment using the decoction at a reduced dosage (every other day treatment), she had a complete recovery (15). 6 years later (at age of 14 years), the patient came back for a follow-up. She was completely normal, and was an outstanding student in her class (middle school) (note: this follow-up result was not in the original publication, was documented in the patient's record in the hospital).

EXAMPLE 6

Treatment of Oliverpontocerebellar Atrophy (Dejerine-Thomas Type, 3 cases) (17)

There are two types of oliverpontocerebellar atrophy: hereditary (Menzel type) and sporadic (Dejerine-Thomas type). All three cases treated here belong to the latter and had failed long-term conventional treatment elsewhere (both Western and Chinese Medicines). The followings are reports of the three cases.

Treatment strategy; Oral intake of BuNaoGao, 2 cubes/day. No additional medication was used.

Case #1: 40-year-old male with a 4-year history. Notable effect was achieved after 100 day's treatment.

Case #2: 47-year-old male with a 2-year history. Notable effect was achieved after 120 day's treatment, Case #3: 60-year-old female with a 3-year history. Notable effect was achieved after 30 day's treatment.

EXAMPLE 7

Treatment of Hereditary Cerebellar Ataxia (3 cases) (18)

All three cases treated have failed long-term conventional treatment elsewhere (both Western and Chinese Medicines).

Treatment strategy: Oral intake of BuNaoGao, 2 cubes/day. No additional medication was used.

Case #1: 23-year-old male with two-year history. Notable effect was achieved after 30 day's treatment.

Case #2: 48-year-old Female with five-year history. Notable effect was achieved after 60 day's treatment.

Case #3: 75-year-old male with one-year history. Notable effect was achieved after 30 day's treatment.

EXAMPLE 8

Treatment of Dementia

Many patients (mainly as outpatients) with senile dementia were treated with BuNaoGao. Significant improvements have been observed in many of these patients, detailed information will become available later on or upon request. Over 50 patients with dementia caused by apoplepxy were also treated with BuNaoGao with satisfactory effect. Detailed result can be further entered later or upon request.

EXAMPLE 9

Treatment of 52 Patients with Sequel of Apoplexy with Fe-Shou-Yi-Qi-Ho-Xie" Decoction for (19).

Satisfactory therapeutic efficacy was observed with this self-designed decoction and its various modifications used. The decoctions reported here lacked one of the core ingredients in the currently applied formulation- "the BuNaoGao" formulation. And additional components, which were not used in "the BuNaoGao" formulation, were also added. Other case reports using similar principle had demonstrated satisfactory results (20-22). The currently applied formulation- "the BuNaoGao" formulation have all the key ingredient for achieving above clinical effect, also based on the inventor's experience of using BuNaoGao (cube form or decoction) in some patients with similar conditions, the currently applied formulation is therefore considered potentially as effective as the decoction reported for treating this type of conditions.

EXAMPLE 10

Treatment of 50 Patients of Apoplexy Combined with Pseudo-Bulbar Palsy (22).

Dysphasia (Gou Yin Bu Quan):
Total effective rate 98% (notable effect 58%)
Dysphagia (Tuen Yian Kun Nan) and choking:
Total effective rate 98% (notable effect 94%)

The decoction reported here lacked one of the core ingredients in the currently applied formulation- "the BuNaoGao" formulation. And additional components, which were not used in "the BuNaoGao" formulation, were also added. This study reflected one of the early attempts by the inventor to define a therapeutic rule (or consensus formulation) for treating this type of disease. The currently applied formulation- "the BuNaoGao" formulation have all the key ingredient for achieving above clinical effect, and is therefore expected to be potentially as effective as the decoction reported.

EXAMPLE 11

Treatment of Encephalopathy

Case #1: sequel of toxic encephalopathy (five months) (23)
Patient: A 5-year-old boy (administration # 71928) Dementia, aphasia, could not stand or walk, very low intelligence (DQ=13). After hospitalization, he was treated with BuNaoGao (one cube/day). 10 days after treatment, he was able to walk with just a little assistance by others; 1 month later, he could walk by himself for 1-2 steps, could say "mum"; 2 month later, he could walk more steadily, and could walk for five meters on his own, muscle strength of both lower limbs $IV^+$. He was considered to have made a notable improvement and was discharged from the hospital.
Case #2: Delayed encephalopathy caused by carbon monoxide poisoning (1 month) (internal record of the hospital)
Patient: A 63-year-old male with a prior history of carbon-monoxide poisoning for one month. He was in a state of coma with frequent convulsion of extremities; EEG showed severe abnormality and CT revealed brain atrophy. After BuNaoGao (2 cubes/day) treatment for 2 weeks, he regained consciousness, and could recognize people, but still had aphasia; One month after BuNaoGao, he could speak simple words; 2 months after BuNaoGao, he could walk by himself, also he could speak fluently and answer questions correctly. EEG and brain CT all returned to normal.

EXAMPLE 12

Treatment of Multiple Sclerosis (MS)

More than three cases of patients with multiple sclerosis have been treated. More complete information regarding these patients will be entered at a later stage or upon request Case #1: A 50-year-old male patient with a 2-year history, and worsening condition for two months (24).

Significant clinical improvement was observed after treatment for 30-35 days using a decoction that bore some resemblance to BuNaoGao. However, it lacked one of the core ingredient of BuNaoGao, and many non-BuNaoGao ingredients were also used at various points. This patient did not have any relapse during the follow-up period of one and half-years. This report reflected one of the early attempts by the inventor to define a therapeutic rule (or consensus formulation) for treating this type of disease.

Case #2. A female outpatient in her early twenties diagnosed with multiple sclerosis by other hospitals (also by the inventor): Within the one year before BuNaoGao was used, she had 5-6 relapses, and was severely handicapped and was in serious condition. After taking BuNaoGab (similar to Example 1) alone for two weeks, she started showing significant clinical improvements. She took BuNaoGao on a daily basis for 2 years, and then on a 2-3-times/week basis. Being followed up by the inventor for the last 8 years, she has not had a single relapse ever since (only one minor fluctuation which may not be qualified as a relapse). Although still feeling weak at times, she was able to resume normal work and normal life (unpublished information).

Case #3. A male Caucasian patient in his late fifties with the non-relapsing type of MS with lower limb involvement (require a cane for slow walking in the house) was treated with BuNaoGao full dosage for one year. No significant progression was observed during the one year when he was on full dosage and the subsequent 1.5 year follow up when he stopped BuNaoGao. By the time of 1.5 year follow up, he needed a walker to walk around the house. Lower limb remains the only limb involved (unpublished information)

EXAMPLE 13

Treatment of Myelitis (25-26).

Case #1: Acute myelitis (26)
Patient: A 37-year-old female, weakness of lower limbs and urine retention for 6 days. The patient had a cold two weeks prior the weakness. BuNaoGao (the cube/tar form, example 1 of the current application) was given at a 2-cubes/day dosage. On the 6th days of BuNaoGao treatment, urine retention was resolved, and urethral catheter was removed; On the 10th day after BuNaoGao, she could walk on flat ground with a cane; on $20^{th}$ day after BuNaoGao, she could walk freely with a normal gait, and could walk up and down stairs without aid, the muscle strength of four limbs reached grade V, but the painful sensation around waist somewhat remained. She continued to be on BuNaoGao for another two months, and clinical cure was achieved in this patient.

Case #2: Sequel of neuromyelitis optica (Devic disease, note by the translator) (25).

Patient: A 27-year-old female patient with one-year history. Clinical cure was achieved in this patient after 27 day's treatment using a decoction that bore some resemblance to BuNaoGao. However, this formulation did not have the consensus of this current BuNaoGao application, and many additional ingredients were also included at various points. Although no well-controlled clinical trial was conducted on myelitis of all types, based on the experience and the theory of the inventor, it is predicted that the currently applied formulation should have therapeutic effect on this type of disease.

EXAMPLE 14

Treatment of Polyneuritis (Polyneuropathy)

14. 1-Case Report (16)

Patient: A 59-year-old male. 6 month's prior, he started experiencing numbness of hands and feet, with a slightly painful sensation. He was afraid of cold and his condition got worse when encountered coldness. He failed other treatments of Western and Chinese Medicines. He had no history of severe illness or drug intake. Examination: in addition to hand and feet numbness, his hands and feet were cold, his whole body was weak. Neurological examination:

weakness of hands and feet; slightly lower muscle tone in four limbs; hypoactive tendon reflexes; reduced sensory to pain, touch and temperature below the ½ of all forelimbs; reduced sensory to sound at angles and wrist. Diagnosis: polyneuritis. Clinical cure was achieved after a one-month treatment with decoctions of Chinese medicine.

Decoctions used for this patient at various points eventually had used all ingredients comprised in the current BuNaoGao formula, and several non-BuNaoGao ingredients were also used. It was then believed that the currently applied formulation should have a beneficial effect on this disease as well as all other types of polyneuritis.

14.2 A Clinical Study of BuNaoGao Effect on Peripheral Polyneuritis (28)

54 cases were hospitalized and treated with BuNaoGao using the standard dosage of 2 lozenges/day, for 1-3 months.

Control group of 36 cases were treated with HuangQiGuiZhiTang (HuangQiGuizhiWuWuTang). 1 standard dosage per day, for 1-3 months. Control group treatment also combined with multiple vitamins.

TABLE 14.1

BuNaoGao effect on Peripheral Polyneuritis

| | Case | Cured | Improved | No effect | Total Effective Rate (%) |
|---|---|---|---|---|---|
| BuNaoGao group | 54 | 25 (46%) | 26 (48%) | 3 (5%) | 51 (94.5%) |
| Control group | 36 | 9 (25%) | 18 (50%) | 9 (25%) | 27 (75%) |

The above result demonstrated therapeutic efficacy of BuNaoGao for peripheral polyneuritis in a controlled study. BuNaoGao result is significantly better than the control treatment group ($P<0.01$).

REFERENCES

1. Xia, YongChao; Li, YianYi; Han, Yian; Xu, WenKe; Dou, YouYi; Zhu, YaPing; Zhang, MinSi; Lu, ShaoMin; Yang, YongShen; Hu, MinLi; Wu, QuanYen; Luo, Ling; Yian, XiaoXia; 1994. Clinical study of BuNaoGao in the treatment of paralysis resulting from head trauma (a trial of 66 cases). Collected in the special issue "Clinical and Basic research of BuNaoGao in the treatment of head injury and children mental retardation" distributed by the Provincial Hospital of Chinese Medicine,Lanzhou, GanSu Province, P. R. China.
2. Xia, YongChao; Li, YianYi; Han, Yian; Xu, WenKe; Dou, YouYi; Zhu, YaPing; Zhang, MinSi; Lu, ShaoMin; Yang, YongShen; Wu, QuanYen; Hu, MinLi; Luo, Ling; Yian, XiaoXia. Clinical study of BuNaoGao in the treatment of 23 patients with motor neuron disease. Chinese Technology Journal of Chinese Medicine (Zhong Guo Zhong Yi Yiao Ke Ji). 1996, 3 (5): 43-. Also 1994, collected in the special issue "Clinical and Basic research of BuNaoGao in the treatment of head injury and children mental retardation" distributed by the Provincial Hospital of Chinese Medicine, Lanzhou, GanSu Province, P. R. China.
3. Xia YbngChao, 1998, BuNaoGao Chinese patent (CN 1182603A) granted in China for a formulation of Chinese Medicine
4. Xia YongChao, Herbal Composition For Treatment Of Neuronal Injuries And Neuronal Degeneration, Methods To Prepare The Same And Uses Thereof. U.S. Ser. No. 10/442865, filed May 22, 2003. Continuation of international application No. PCT/IB01/02859. U.S. patent approved Dec 2006.
5. Xia, YongChao et al, 1994, "Clinical and Basic research of BuNaoGao in the treatment of head injury and children mental retardation". A collection of reports submitted for peer review process for regulatory approval of BuNaoGao. This special report is distributed by the Provincial Hospital of Chinese Medicine, LanZhou, GanSu Province, P. R. China.
6. Meininger et al., Pentoxifylline European Group. Pentoxifylline in ALS: a double-blind, randomized, multicenter, placebo-controlled trial. Neurology. 2006 Jan. 10;66 (1): 88-92.
7. Miller et al., Riluzole for amyotrophic lateral sclerosis (ALS)/motor neuron disease (MND). Cochrane Database Syst Rev. 2007 Jan. 24; (1):CD001447.
8. Bensimon et al., A controlled trial of riluzole in amyotrophic lateral sclerosis. ALS/Riluzole Study Group. N Engl J Med. 1994 Mar. 3;330 (9):585-91.
9. Lacomblez et al., Dose-ranging study of riluzole in amyotrophic lateral sclerosis. Amyotrophic Lateral Sclerosis/ Riluzole Study Group II. Lancet. 1996 May 25;347 (9013): 1425-31.
10. Xia, YongChao; Li, YianYi; Han, Yian; Lu,ShaoMin; Yang, YongShen; Xu, WenKe; Dou, YouYi; Zhu, YaPing; Zhang, MinSi; Hu, MinLi; Wu, QuanYen; Yian, XiaoXia; Luo, Ling. Jin, WenMei. 1994. Clinical study of BuNaoGao in the treatment of children with mental retardation (a trial of 133 cases). Collected in the special issue "Clinical and Basic research of BuNaoGao in the treatment of head injury and children mental retardation" distributed by the Provincial Hospital of Chinese Medicine,Lanzhou, GanSu Province, P. R. China.
11. Xia, YongChao; Li, YianYi; Han, Yian; Yang, YongShen; Lu, ShaoMin; Xu, WenKe; Dou, YouYi; Zhang, MinSi; Zhu, YaPing; Wu, QuanYen; Hu, MinLi; Yian, XiaoXia; Luo, Ling. Jin, WenMei. 1994. Clinical study of BuNaoGao in the treatment of children with cerebral palsy (a trial of 102 cases). Collected in the special issue "Clinical and Basic research of BuNaoGao in the treatment of head injury and children mental retardation" distributed by the Provincial Hospital of Chinese Medicine,LanZhou, GanSu Province, P. R. China.

12. Xia, YongChao et al., (case report prepared by Yang, YongShen). Illustration of typical cases of amyotrophic lateral sclerosis-ALS: Case #8. 1994, Collected in the special issue "Clinical and Basic research of BuNaoGao in the treatment of head injury and children mental retardation" distributed by the Provincial Hospital of Chinese Medicine, GanSu Province, P. R. China. (Administration number #69834).

13. Xia, YongChao et al, 1994. (case report prepared by Lu, ShaoMin). Illustration of typical cases of amyotrophic lateral sclerosis-ALS: Case #9. (Administration number #73819). Collected in the special issue "Clinical and Basic research of BuNaoGao in the treatment of head injury and children mental retardation" distributed by the Provincial Hospital of Chinese Medicine, GanSu Province, P. R. China.

14. Xia, YongChao, Li YianYi. 1992. Case report of one patient with primary lateral sclerosis. New Journal of Traditional Chinese Medicine (Xin ZhongYi). 24 (6):22.

15. Xia,YongChao. Clinical cure of one case with severe paralysis (post-encephalitis type B) using "Fo-Shou-Bu-Sui" decoction. Journal of Chinese Medicine (ZhongYi Za Zhi) 1989.4: 40.

16. Xia, YongChao. BuNaoGao in the treatment of two patients in vegatative states. 1994
    Collected in the special issue "Clinical use of BuNaoGao in the treatment of brain damage and children mental retardation and experimental studies" distributed by the Provincial Hospital of Chinese Medicine, Lanzhou, GanSu Province, P. R. China.

17. Xia, YongChao; Han, Yian; Zhang, MinShi and Li, YianYi. BuNaoGao for the treatment of Oliverponto-cerebellar atrophy (Dejerine-Thomas type, 3 cases). *China College Journal of Medicine* (Zhong Guo Yi Yiao Xue Xue Bao) 1992, 6. Also collected in the special issue "Clinical and Basic research of BuNaoGao in the treatment of head injury and children mental retardation", 1994. distributed by the Provincial Hospital of Chinese Medicine, Lanzhou, GanSu Province, P. R. China.

18. Yang,YongSheng; Han,Yian; Xia,YongChao. BuNaoGao for the treatment of hereditary cerebellar ataxia (3 cases)
    Collection of the Second China Conference on Difficult and Complicated diseases, 1994: June at Bei-Dai-He. Also collected in the special issue "Clinical and Basic research of BuNaoGao in the treatment of head injury and children mental retardation", distributed by the Provincial Hospital of Chinese Medicine, Lanzhou, GanSu Province, P. R. China.

19. Xia,YongChao; Xu, WenKe; Li,YianYi; Han,Yian; Dou, YouYi; Zhu, YaPing; Zhang,MinSi; Lu,ShaoMin; 1991. "Fe-Shou-Yi-Qi-Ho-Xie" decoction for the treatment of 52 patients with sequel of apoplexy. Chinese Journal of Integrated Traditional and Western Medicine (Zhong Xi Yi Jie He Zazhi), 12:736

20. Xia, YongChao. Treatment of one patient with post-apoplexy tremor. Tianjin Journal of Traditional Chinese Medicine (TianJin ZhongYi). 1990, 6: 12.

21. Xia,YongChao. 1990. Treatment of stroke with an emphasized use on Radix angelica sinensis. YunNan College Journal of Chinese Medicine (YunNan ZhongYi XueYuan XueBao), 13 (1): 29.

22. Xia, YongChao; Li, YianYi; Han, Yian; Xu, WenKe; Zhu, YaPing; Dou, YouYi; Zhang, MinSi; Lu,ShaoMin; Luo, Ling. 1993. Clinical study of 50 cases of apoplexy combined with pseudo-bulbar palsy. Journal of Traditional Chinese Medicine (ZhongYi ZaZhi), 4, 227.

23. Xia, YongChao et al, 1994. One patient with sequel of toxic encephalopathy (five months). (case report prepared by Yang, YongSheng). Illustration of typical cases: Case #7 (Toxic encephalopathy). Collected in the special issue "Clinical and Basic research of BuNaoGao in the treatment of head injury and children mental retardation" distributed by the Provincial Hospital of Chinese Medicine, Lanzhou, GanSu Province, P. R. China.

24. Xia, YongChao. 1989. Clinical experience of treating one patient with Multiple Sclerosis. Beijing Journal of Chinese Medicine (Beijing Zhong Yi Za Zhi). 3:41.

25. Xia,YongChao. 1990 Sequel of neuromyelitis optica (Devic disease, note by the translator). SiChuan Journal of Chinese Medicine (SiChuan ZhongYi Zazhi). 2: 41.

26. Li, YianYi; Xia, YongChao. 1994. Clinical cure of one patient with acute myelitis by BuNaoGao. Journal of GanSu College of Traditional Chinese Medicine (GanSu ZhongYi XueYuan XueBao). 11 (1), 31.

27. Xia, YongChao. 1989 Clinical experience of treating one case with peripheral polyneuritis Si-Chuan Journal of Chinese Medicine (Si-Chuan Zhong Yi). 6: 37.

28. LuShaoMin, 2003. Clinical observation of BuNaoGao in treating peripheral polyneuritis (polyneuropathy). Chinese journal of information on traditional Chinese medicine. 10: 6.

29. Huang et al., Pharmacological study of BuNaoGao. Journal of Gansu College of Traditional Chinese Medicine (Gansu Zhong Yi Xue Yuan Xue Bao) 1992; 9 (2): 27-31.

30. YongChao Xia, 1996. Application of formulation from "Finger citron powder therapeutic series" in the treatment of brain and spinal cord injury. Experience in the treatment of complicated diseases/syndromes.
    Published by Pulisher of Chinese medicine literature (ZhongYi GuJi publisher) Vol. 1, page 330.

31. Xia, YongChao et al, Clinical study of BuNaoGao in the treatment of paralysis caused by head trauma. 1996. China Chinese medicine press (Zhong Gu ZhongYi Yiao Chu Ban She), May Volume, p 342.

32. Xia, YongChao et al, 1996. Clinical and Basic research of BuNaoGao in the treatment of head injury and children mental retardation. China Chinese medicine press (Zhong Gu Zhong Yi Yiao Chu Ban She), Volume 1.

33. Xia, YongChao; Li, YianYi; Han, Yian; Yang, YongShen; Lu, ShaoMin; Ku, WenKe; Dou, YouYi; Zhang, MinSi; Zhu, YaPing; Wu, QuanYen; Hu, MinLi; Yian, XiaoXia; Luo, Ling. Jin, WenMei. 1996. Clinical study of BuNaoGao in the treatment of children with cerebral palsy (a trial of 102 cases). Recovery of Children with disability (Chan Ji Er Tong Kang Fu), volume 3-4, page 33-.

34. Xia, YongChao; Li, YianYi; Han, Yian; Lu,ShaoMin; Yang, YongShen; Xu, WenKe; Dou, YouYi; Zhu, YaPing; Zhang, MinSi; Hu, MinLi; Wu, QuanYen; Yian, XiaoXia; Luo, Ling. Jin, WenMei. 1996. Clinical study of BuNaoGao in the treatment of children with mental retardation (a trial of 133 cases). Recovery of Children with disability (Chian Ji Er Tong Kang Fu), volume 3-4, page 37-.

35. Xia, YongChao et al. Clinical and Basic research of BuNaoGao in the treatment of head injury and children mental retardation. China Chinese Medicine Press, 1996, may, first print, page 106.

What is claimed is:

1. A method of treating head or spinal cord injuries, comprising the step of administering to a patient in need thereof a compositing consisting essentially of

*Radix angelica sinensis* (DangGui) 0.82.-3.3 g/kg body weight, *Ligusticum chuanxiong* (ChuanXiong) 0.1-1.2 g/kg body weight, *Hirudo* (ShuiZhi) 0.1-0.4 g/kg body weight, *Polygonatum sibiricum* (HuangJing) 0.2-0.8 g/kg body weight, *Glycyrrhiza uralensis* (Gancao) 0.06-0.21 g/kg body weight, *Astragalus membranaceus* (HuangQi) 0.315 g-1.2 g/Kg body weight, *Curculigo orchioides* (XianMao) 0.1-1 g/Kg body weight, *epimedium grandiflorum* (YinYangHuo) 0.1-1 g/Kg body weight, *Psoralea corylifolia* (Bucuzhi) 0.1-1 g/Kg body weight, *Leonurus heterophyllus* (YiMucao) 0.1-1 g/Rg body weight, and *Paeonia rubrae* (Chishao) 0.1-1 g/Kg body weight, wherein the g/kg body weight dosages can be increased up to 2.5 times if the body weight of the patient is less than 40 kg.

2. The method of claim 1, wherein *Ligusticum chuanxiong* (ChuanXiong) is replaced by *Carthamus tinctorius* (Hong Hua) 0.1-1.2 g/kg body weight.

3. The method of claim 1, wherein the composition is administered daily.

4. A method of treating head or spinal cord injuries, comprising the step of administering to a patient in need thereof a compositing consisting essentially of

*Radix angelica sinensis* (DangGui) 0.82-3.3 g/kg body weight, *Ligusticum chuanxiong* (ChuanXiong) 0.1-1.2 g/kg body weight, *Hirudo* (ShuiZhi) 0.1-0.4 g/kg body weight, *Polygonatum sibiricum* (HuangJing) 0.2-0.8 g/kg body weight, *Glycyrrhiza uralensis* (Gancao) 0.06-0.21 g/kg body weight, *Astragalus membranaceus* (HuangQi) 0.315 g-1.2 g/Kg body weight, *Lycium chinensis mill* (GouQiZi) 0.1-1 g/Kg body weight, *Curculigo orchioides* (XianMao) 0.1-1 g/Kg body weight, *epimedium grandiflorum* (YinYangHuo) 0.1-1 g/Kg body weight, *Cornus officinalis* (ShanZhuYu) 0.1-1 g/Rg body weight, *Psoralea corylifolia* (BuGuZhi) 0.1-1 g/Kg body weight, *Leonurus heterophyllus* (YiMucao) 0.1-1 g/Kg body weight, and *Paeonia rubrae* (Chishao) 0.1-1 g/Kg body weight, wherein the g/kg body weight dosages can be increased up to 2.5 times if the body weight of the patient is less than 40 kg.

5. The method of claim 4, wherein *Ligusticum chuanxiong* (ChuanXiong) is replaced by *Cartharnus tinctorius* (Hong Hua) 0.1-1.2 g/kg body weight.

6. The method of claim 4, wherein the composition is administered daily.

* * * * *

UNITED STATES PATENT AND TRADEMARK OFFICE
CERTIFICATE OF CORRECTION

PATENT NO. : 7,416,747 B2 Page 1 of 1
APPLICATION NO. : 11/735101
DATED : August 26, 2008
INVENTOR(S) : YongChao Xia It is certified that error appears in the above-identified patent and that said Letters Patent is hereby corrected as shown below:

In column 2, line 11, "Chinese Patent Application No. 199119227.3, Mar.8, 2000, Zhan" should be -- Chinese Patent Application No. 99119227.3, Mar. 8, 2000, Zhan --

Signed and Sealed this

Twenty-first Day of October, 2008

JON W. DUDAS
*Director of the United States Patent and Trademark Office*